US007026467B2

(12) United States Patent
Keim et al.

(10) Patent No.: US 7,026,467 B2
(45) Date of Patent: Apr. 11, 2006

(54) **HIGH RESOLUTION TYPING SYSTEM FOR PATHOGENIC *MYCOBATERIUM TUBERCULOSUM***

(75) Inventors: Paul S. Keim, Flagstaff, AZ (US); Robert Scott Spurgiesz, Flagstaff, AZ (US); James M. Schupp, Flagstaff, AZ (US)

(73) Assignee: Arizona Board of Regents, acting for and on behalf of, Northern Arizona University, Tempe, AZ (US)

(*) Notice: Subject to any disclaimer, the term of this patent is extended or adjusted under 35 U.S.C. 154(b) by 121 days.

(21) Appl. No.: 10/624,714

(22) Filed: Jul. 21, 2003

(65) Prior Publication Data

US 2004/0121366 A1 Jun. 24, 2004

Related U.S. Application Data

(60) Provisional application No. 60/397,224, filed on Jul. 19, 2002.

(51) Int. Cl.
*C07H 21/04* (2006.01)
*C07H 19/00* (2006.01)
*A61K 39/04* (2006.01)

(52) U.S. Cl. ................ 536/24.3; 424/184.1; 424/190.1; 424/234.1; 424/248.1; 435/4; 435/6; 435/91.2; 536/22.1; 536/23.1

(58) Field of Classification Search .............. 424/184.1, 424/190.1, 234.1, 248.1; 435/4, 6, 91.2; 536/22.1, 536/23.1, 24.3
See application file for complete search history.

(56) References Cited

U.S. PATENT DOCUMENTS

| | | | | |
|---|---|---|---|---|
| 4,683,195 A | | 7/1987 | Mullis et al. | |
| 4,683,202 A | | 7/1987 | Mullis | |
| 6,228,371 B1 | * | 5/2001 | Nano | 424/248.1 |
| 6,270,973 B1 | | 8/2001 | Lewis et al. | |
| 6,294,328 B1 | * | 9/2001 | Fleischmann et al. | 435/6 |
| 6,449,562 B1 | | 9/2002 | Chandler et al. | |
| 6,479,235 B1 | | 11/2002 | Schumm et al. | |

FOREIGN PATENT DOCUMENTS

| | | | |
|---|---|---|---|
| WO | WO 97/44463 | * | 11/1997 |
| WO | WO 99/09186 | * | 2/1999 |
| WO | WO 01/02568 | * | 1/2001 |
| WO | WO 01/35317 | * | 5/2001 |

OTHER PUBLICATIONS

Genbank, #AAF66212, search for SEQ ID No:6, Williams et al, WO 01/02568.*

Genbank, search for SEQ ID No:12, Fleischman et al, U.S. Pat. No. 6294328.*

. . . , "Global Tuberculosis Control Report", World Health Organization, p. 6, 2002.

Bifani, P., et al., "Global dissemination of the *Mycobacterium tuberculosis* W family strains", article, Trends in Microbiology 10:45–52, 2002.

Braden, C., et al., "Assessment of *Mycobacterium tuberculosis* Genotyping in a Large Laboratory Network", article, Emerging Infec Diseases 8(11):1210–5, Nov. 2002.

Castro, K., et al., "Rationale and methods for the national tuberculosis genotyping and surveillance network", article, Emerging Infec Diseases 8:(11)88–91, 2002.

Cowen, L., et al., "Variable–Number Tandem Repeat Typing *Mycobaterium tuberculosis* Isolates with Low Copy Numbers of SI6110 by Using Mycobacterial Interspersed Repetitive Units", article. J Clin Microb 40–1592–602. 2002.

Dale, J., et al., "Spacer oligonucleotide typing of *Mycobacterium tuberculosis*: recommendations for standardized nomenclature"article, Int J Tuberc Lung Dis, 5:216–19, 2001. (abstract).

Fang, Z., et al., "Molecular evidence for independent occurence of IS6110 insertions at the same sites to the genome of *Mycobacterium tuberculosis* in different clinical isolates", article, J Bacertiol 183:5279–5284[redacted] , 2001.

Farlow, J., et al., "Francisella tularensis strain typing using multiple–locus, variable–number tandem repeat analysis", article, J Clin Microb, 39:3186–92, 2001.

Frothingham, R., et al., "Genetic diversity in the *Mycobacterium tuberculosis* complex based on variable numbers of tandem DNA repeats", article, Microbiology 144:1189–96, 1998.

Kamerbeek, J., et al., "Simultaneous detectin and strain differentiation of *Mycobacterium tuberculosis* for diagnosis and epidemiology", article, J Clin Microbiol 35:907–14, 1997.

Keim, P., et al., "Multiple–locus variable–number tandem repeat analysis reveals genetic relationships within *Bacillus anthracis*", article, J of Bacteriol 182:2928–36, 2000.

Kremer, K., et al., Comparison of methods based on different molecular epidemiological markers for typing of *Mycobacterium tuberculosis* complex strains: Interlaboratory study of discriminatory power and reproducibility. J Clin Microbiol 37:2607–18, 1999.

(Continued)

*Primary Examiner*—Rodney P Swartz
(74) *Attorney, Agent, or Firm*—Robert D. Atkins; Quarles & Brady Streich Lang LLP

(57) ABSTRACT

MLVA methods for strain discrimination among *Mycobacterium tuberculosum* strains are disclosed. Nine VNTR loci have been identified from genomic sequences of *Mycobacterium tuberculosum* strains and primer pairs suitable for amplifying the VNTR by PCR are disclosed. Polymorphisms at these loci were used to resolve genotypes into distinct groups. This sub-typing scheme is useful for the epidemiological study of *Mycobacterium tuberculosum* and may be applied to the local detection of the pathological causative agent of *tuberculosum.*

4 Claims, 3 Drawing Sheets

OTHER PUBLICATIONS

Le Fleche P. et al., "High resolution, on–line identification of strains from the *Mycobacterium tuberculosis* complex based on tandem repeat typing". BMC Microbiol. 37:1–12, 2002.

Mazars, E. et al., "High–resolution minisatellite–based typing as a portable approach to global analysis of *Mycobacterium tuberculosis* molecular epidemiology", Proceedings of Natl Acad Sci US 98:1901–6, 2001.

Quitugua, T. et al., "Transmission of drug resistant tuberculosis in Texas". J Clin Microbiol. 40:8. 2716–24, 2002.

Skuce, R. et al., "Discrimination of *Mycobacterium tuberculosis* complex bacteria using novel VNTR–PCR targets". Microbiology. 148:519–28. 2002.

Sola, C. et al., "Spoligotype database of *Mycobacterium tuberculosis*: biogeographic distribution of shared types and epidemiologic and phylogenetic perspectives". Emerging Infectious Diseases. 7:390–6. 2001.

Sola, C. et al., "*Mycobacterium tuberculosis* phylogeny reconstruction based on combined numerical analysis with IS1081, IS6110, VNTR, and DR–based spoligotyping suggests the existence of two new phlyogeographical clades". J Molecr Ev. 53:680–9. 2001.

Supply, P. et al., "Automated high–throughput genotyping for study of global epidemiology of *Mycobacterium tuberculosis* based on mycobacterial interspersed repetitive units", J Clin Microbiol 39:3563–71. 2001.

Supply, P. et al., "Identification of novel intergenic repetitive units in a mycobacterial two–component system operon". Molec Microbiol. 26:991–1003. 1997.

Supply, P. et al., "Variable human minisatellite–like regions in the *Mycobacterium tuberculosis* genome". Molec Microbiol. 36:762–71. 2000.

van Embden, J. et al., "Strain identification of *Mycobacterium tuberculosis* by DNA fingerprinting: recommendations for a standardized methodology". J Clin Microbiol 31:406–9. 1993.

Van Soolingen, D., "Molecular epidemiology of tuberculosis and other mycobacterial infections: main methodologies and achievements". J Inter Med. 249:1–26. 2001.

Genbank, ID#AAH51958, search for SEQ ID NO:1 and 2, Eisenberg et al, WO 01/35317.*

Genbank, ID#AAX34004, search for SEQ ID NO:3 and 4, Gicquel et al, WO 99/09186.*

Genbank, A67694, search for SEQ ID NO:7 and 8, Menozzi et al WO 97/44463.*

Genbank, AR14509/c, search for SEQ ID NO:15 and 16, Nano et al, 6,228,371.*

Genbank, #AAF66212, search for SEQ ID NO:6, Williams et al, WO 01/02568.*

Genbank, search for SEQ ID NO:12, Fleischman et al, U.S. Pat. No. 6294328.*

* cited by examiner

SEQUENCE LISTING

```
<160> NUMBER OF SEQ ID NOS: 27

<210> SEQ ID NO 1
<211> LENGTH: 27
<212> TYPE: DNA
```

-continued

```
<213> ORGANISM: Artificial Sequence
<220> FEATURE:
<223> OTHER INFORMATION: Mycobacterium tuberculosum primer

<400> SEQUENCE: 1

gtcgaacgag actttcccca aaccgac                                      27


<210> SEQ ID NO 2
<211> LENGTH: 24
<212> TYPE: DNA
<213> ORGANISM: Artificial Sequence
<220> FEATURE:
<223> OTHER INFORMATION: Mycobacterium tuberculosum primer

<400> SEQUENCE: 2

gaccgtgggc tggatgacgg tctc                                         24


<210> SEQ ID NO 3
<211> LENGTH: 26
<212> TYPE: DNA
<213> ORGANISM: Artificial Sequence
<220> FEATURE:
<223> OTHER INFORMATION: Mycobacterium tuberculosum primer

<400> SEQUENCE: 3

gatgacggat cgtcgggggc gggaac                                       26


<210> SEQ ID NO 4
<211> LENGTH: 30
<212> TYPE: DNA
<213> ORGANISM: Artificial Sequence
<220> FEATURE:
<223> OTHER INFORMATION: Mycobacterium tuberculosum primer

<400> SEQUENCE: 4

gcaacgcgag ggcgatcagt actgccaaca                                   30


<210> SEQ ID NO 5
<211> LENGTH: 28
<212> TYPE: DNA
<213> ORGANISM: Artificial Sequence
<220> FEATURE:
<223> OTHER INFORMATION: Mycobacterium tuberculosum primer

<400> SEQUENCE: 5

gctgtggcgc agctacacag tacgactc                                     28


<210> SEQ ID NO 6
<211> LENGTH: 21
<212> TYPE: DNA
<213> ORGANISM: Artificial Sequence
<220> FEATURE:
<223> OTHER INFORMATION: Mycobacterium tuberculosum primer

<400> SEQUENCE: 6

gattgcgcag cgcccaacag c                                            21


<210> SEQ ID NO 7
<211> LENGTH: 24
<212> TYPE: DNA
<213> ORGANISM: Artificial Sequence
<220> FEATURE:
<223> OTHER INFORMATION: Mycobacterium tuberculosum primer

<400> SEQUENCE: 7

ggaggcgttg ggtacggtcg catc                                         24
```

-continued

<210> SEQ ID NO 8
<211> LENGTH: 26
<212> TYPE: DNA
<213> ORGANISM: Artificial Sequence
<220> FEATURE:
<223> OTHER INFORMATION: Mycobacterium tuberculosum primer

<400> SEQUENCE: 8
gattcggagc ccgactactt ctgggt 26

<210> SEQ ID NO 9
<211> LENGTH: 24
<212> TYPE: DNA
<213> ORGANISM: Artificial Sequence
<220> FEATURE:
<223> OTHER INFORMATION: Mycobacterium tuberculosum primer

<400> SEQUENCE: 9
cgccgacgag gccgatgccg aagc 24

<210> SEQ ID NO 10
<211> LENGTH: 25
<212> TYPE: DNA
<213> ORGANISM: Artificial Sequence
<220> FEATURE:
<223> OTHER INFORMATION: Mycobacterium tuberculosum primer

<400> SEQUENCE: 10
ccgcggcggc agagccaacc aggat 25

<210> SEQ ID NO 11
<211> LENGTH: 20
<212> TYPE: DNA
<213> ORGANISM: Artificial Sequence
<220> FEATURE:
<223> OTHER INFORMATION: Mycobacterium tuberculosum primer

<400> SEQUENCE: 11
cgaggcgccc agccccacaa 20

<210> SEQ ID NO 12
<211> LENGTH: 27
<212> TYPE: DNA
<213> ORGANISM: Artificial Sequence
<220> FEATURE:
<223> OTHER INFORMATION: Mycobacterium tuberculosum primer

<400> SEQUENCE: 12
cacccgcgct ttaggatcga cacctga 27

<210> SEQ ID NO 13
<211> LENGTH: 20
<212> TYPE: DNA
<213> ORGANISM: Artificial Sequence
<220> FEATURE:
<223> OTHER INFORMATION: Mycobacterium tuberculosum primer

<400> SEQUENCE: 13
gcgccgcacc acctcgactt 20

<210> SEQ ID NO 14
<211> LENGTH: 22
<212> TYPE: DNA
<213> ORGANISM: Artificial Sequence
<220> FEATURE:

-continued

<223> OTHER INFORMATION: Mycobacterium tuberculosum primer

<400> SEQUENCE: 14
ccgggcaaaa cctccgccta ac 22

<210> SEQ ID NO 15
<211> LENGTH: 26
<212> TYPE: DNA
<213> ORGANISM: Artificial Sequence
<220> FEATURE:
<223> OTHER INFORMATION: Mycobacterium tuberculosum primer

<400> SEQUENCE: 15
acaacggcga ggcccgaatc tacgaa 26

<210> SEQ ID NO 16
<211> LENGTH: 19
<212> TYPE: DNA
<213> ORGANISM: Artificial Sequence
<220> FEATURE:
<223> OTHER INFORMATION: Mycobacterium tuberculosum primer

<400> SEQUENCE: 16
gtcgacgccg ccgatgacc 19

<210> SEQ ID NO 17
<211> LENGTH: 25
<212> TYPE: DNA
<213> ORGANISM: Artificial Sequence
<220> FEATURE:
<223> OTHER INFORMATION: Mycobacterium tuberculosum primer

<400> SEQUENCE: 17
cccggagggc cagagggcac atagc 25

<210> SEQ ID NO 18
<211> LENGTH: 30
<212> TYPE: DNA
<213> ORGANISM: Artificial Sequence
<220> FEATURE:
<223> OTHER INFORMATION: Mycobacterium tuberculosum primer

<400> SEQUENCE: 18
tggcgcagaa ccaggagtag caccaatgag 30

<210> SEQ ID NO 19
<211> LENGTH: 379
<212> TYPE: DNA
<213> ORGANISM: Artificial Sequence
<220> FEATURE:
<223> OTHER INFORMATION: Mycobacterium tuberculosum amplicon

<400> SEQUENCE: 19
ggctcgggcc tgccgtcgga catctggaag gcaaccatgg acggcgcctt gaagggcacg 60
tcgaacgaga ctttccccaa accgaccgag gtcggtggtt atgccggtgt gccgccgccg 120
ccgccgccgc cggaggtacc accttcgcag accgtcatcc agcccacggt cgaaattgcg 180
ccggggatta ccatcccgat cggtcccccg accaccatta ccctggcgcc accgcccccg 240
gccccgcccg ctgcgactcc cacgccgccg ccgtgaccgg cgcgctgtcc caaagcagca 300
acatctcgcc acttcctttg gccgccgatc tgcggagcgc cgataaccgc gattgcccca 360
gccgcaccga cgtattggg 379

-continued

<210> SEQ ID NO 20
<211> LENGTH: 352
<212> TYPE: DNA
<213> ORGANISM: Artificial Sequence
<220> FEATURE:
<223> OTHER INFORMATION: Mycobacterium tuberculosum amplicon

<400> SEQUENCE: 20
gcgagcctac cgaagatcgc gtgcatgcgt tcggcgtgga ccgcacagca cctggagttg 60
gcggcgccga gggccgagat ggcaggatga ccgatcgtcg ggggcgggaa ctcccaggcc 120
gccgggccgt cgcaaacccg tcgcaaaccc gtcgcaaacc gtaaggagtc atccatgaag 180
acaggcaccg cgacgacgcg gcgcaggctg ttggcagtac tgatcgccct cgcgttgccg 240
ggggccgccg ttgcgctgct ggccgaacca tcagcgaccg gcgcgtcgga cccgtgcgcg 300
gccagcgaag tggcgaggac ggtcggttcg gtcgccaagt cgatgggcga ct 352

<210> SEQ ID NO 21
<211> LENGTH: 512
<212> TYPE: DNA
<213> ORGANISM: Artificial Sequence
<220> FEATURE:
<223> OTHER INFORMATION: Mycobacterium tuberculosum amplicon

<400> SEQUENCE: 21
attcaggccg ccgaatccac taccgatgat gaccacgcga tggcgcccgc cgacggccga 60
gggttcacca gatgagagcg tcatggtcct ccttcagtct ggtcgctgtg gcgcagctac 120
acagtacgac tcccgtcatg ccaacggcgt aactttttgt gggccttgtg ggccttgtgg 180
gccttgtggg cctttgtcgg gccgccttcg gatcggacgc tcgggatggc tgttgggcgc 240
tgcgcaatcc cgcgcttcga tcaggcagcg tccggcagtg ccatcaatgg cggccaggta 300
cacctctccg acggctcgac atcgccggcc cggcagttac ctgcaccatg gccgggcgat 360
gcgggagcgg ctgccgaagg tcgggcaggt gtttgctgcc ggggaaatcg actaccacat 420
gtttcagacg ttggtgtatc gcaccgattt gatcaccgac ccgcaggtgt tggcgcgggt 480
ggatgccgag ctggcgctgc gggtgcgggg ct 512

<210> SEQ ID NO 22
<211> LENGTH: 476
<212> TYPE: DNA
<213> ORGANISM: Artificial Sequence
<220> FEATURE:
<223> OTHER INFORMATION: Mycobacterium tuberculosum amplicon

<400> SEQUENCE: 22
agccagcaga gcttcgagga agtgtcggcg cgcgccgaag gctacgtgga ccaggcggtg 60
gagttgaccc aggaggcgtt gggtacggtc gcatcgcaga cccgcgcggt cggtgagcgt 120
gccgccaagc tggtcggcat cgagctgcct aagaaggctg ctccggccaa gaaggccgct 180
ccggccaaga aggccgctcc ggccaagaag gcggcggcca agaaggcgcc cgcgaagaag 240
gcggcggcca agaaggtcac ccagaagtag tcgggctccg aatcaccatc gactccgagt 300
cgcccacggg gcgactcgga gtcgacgtgt tggatgcaaa ccgcatagtc tgaatgcgtg 360
agccacctcg tgggtaccgt catgctggta ttgctggtcg ccgtcttggt gacagcggtg 420
tacgcgtttg tgcatgctgc gttgcagcgg cccgatgcct ataccgccgc cgacaa 476

<210> SEQ ID NO 23
<211> LENGTH: 551
<212> TYPE: DNA

-continued

<213> ORGANISM: Artificial Sequence
<220> FEATURE:
<223> OTHER INFORMATION: Mycobacterium tuberculosum amplicon

<400> SEQUENCE: 23
gcagaccgca ggtgccgacg agccggacta cttagacgtc gatgtggtcg aagaagactc 60
ggaggcgctt ccggtggggg ctggcgctgc ggtcggcgag tccgccgacg aggccgatgc 120
cgaagctgct gacggagttg cgggccacgc cgacccggag gccgacccgg tcgaatacga 180
atacgaatac gaatacgtcg aggacacctg cggtttggag ctcgaggagg acgaccagga 240
agcgccaccg accgtcgcat ccggcacgtc acggcggcgc cgattcgaca ccaagaccgc 300
cgccgcggtc agcgcccgca agtacacctt ccgcaaacgt gcgttgatcg tgatggcggt 360
gatcctggtt ggctctgccg ccgcggcctt cgagctgacc ccggtcgcgt ggtggatctg 420
tggtagcgcc accggtgtga cggtgctcta cctggcatat ttgcgtcggc aaacccgcat 480
cgaggagaag gtgcgtcggc ggcggatgca gcggatcgcg cgggcgcggc tcggtgtaga 540
gaacacccgt g 551

<210> SEQ ID NO 24
<211> LENGTH: 355
<212> TYPE: DNA
<213> ORGANISM: Artificial Sequence
<220> FEATURE:
<223> OTHER INFORMATION: Mycobacterium tuberculosum amplicon

<400> SEQUENCE: 24
atccttgcag gtgttcggtg gtgacggtcg tgttgtcggc ggcttccagg cgcaaccgga 60
ggcgcccagc cccacaatca gtgccaacag tgccaacagt gccaacagtg ccagaatcgg 120
gacggcgcta cgctgacgac gcacgtcacg agcttagcga aaactgggaa tttcccctac 180
gtttcatcaa cgcctcaggt gtcgatccta aagcgcgggt gccgccggta ttcttgcccc 240
aaatcggtcg gttgacaccc gatgcggtcg gcgaagccat cggcatcgcg gccgacgaca 300
tcccgatggc ggcacgctgg atcggcagcc gaccatgctc gctcatcggc cagcc 355

<210> SEQ ID NO 25
<211> LENGTH: 647
<212> TYPE: DNA
<213> ORGANISM: Artificial Sequence
<220> FEATURE:
<223> OTHER INFORMATION: Mycobacterium tuberculosum amplicon

<400> SEQUENCE: 25
ccgcgccgat cggttccgtt gatccgcgct ccccgcagcc gcgccgtcag atccgcgggc 60
ccggcatcgt ggcggcgcac agcgcggggg tggtgcaccc gaacctcggt gatggtccgg 120
ccggtcacgt gagcctgcaa gccgcgccgc accacctcga cttcgggcag ctcgggcatc 180
cagtgatgat cgcaagcgcg gcgaagccgg gcgcagcggg tcatcaccat cgaaccagtg 240
atgatcgcaa gcgcggcgaa gccgggcgca gcgggtcatc accatcgaac cagtgatgat 300
cgcaagcgcg gcgaagccgg gcgcagtccc ccgcaagcgg gaggtgcccc caggtcatca 360
ccatcgaacc agtgatcatc gcaagcgcgg cgaagccggg cgcagtcccc cccaagcggg 420
aggtgccccc aggtcatcac catcgaacca gtgatgatcg caagcgcggc gaacccggcc 480
gcagtccccc gcaagcgcgg caaagccggc gcccccaggt catcaccatc aatccagtta 540
ggcggaggtt ttgcccggca tggcgttgtc gagcacttcc agggctttcc aagcggccgc 600
cgcggctttt tgctcggctt cttttttgga ccggcccact cctgaac 647

-continued

<210> SEQ ID NO 26
<211> LENGTH: 663
<212> TYPE: DNA
<213> ORGANISM: Artificial Sequence
<220> FEATURE:
<223> OTHER INFORMATION: Mycobacterium tuberculosum amplicon

<400> SEQUENCE: 26
cgggctatca ccggttcatc ttctgggcct atggccgcaa cggggagagc gatcctcggg 60
tactcgaggc catccaagtc ctccgtatcc gctatatcct gaccagcact ccgacggtgc 120
gggggtttgc cgtgccggac ggactagtgt cgttagagac atcgaggtcg tgggcgaaga 180
tctacgacaa cggcgaggcc cgaatctacg aatggcgcgg cactgccgca gcaacacact 240
cctagaaggt gcgtaagagg atggtgattg gattgagtac cggcagcgac gacgacgacg 300
tcgaggtcat cggcggcgtc gacccgcggc tgatagcggt gcaggagaac gactccgacg 360
agtcgtcgct gaccgacctg gtcgagcagc ccgccaaggt gatgcgcatc ggcaccatga 420
tcaagcaact gctcgaggag gttcgcgccg ccccactcga cgaagccagc cgcaatcggc 480
tacgcgatat ccacgccacc agcatccgcg aactcgaaga tggtctggcc ccggaactgc 540
gcgaggagct cgaccggctt accctgccgt tcaacgagga cgccgtgccc tcggacgccg 600
agttgcgcat tgcccaggca cagctggtcg gctggctgga agggctgttc cacggcatcc 660
aaa 663

<210> SEQ ID NO 27
<211> LENGTH: 771
<212> TYPE: DNA
<213> ORGANISM: Artificial Sequence
<220> FEATURE:
<223> OTHER INFORMATION: Mycobacterium tuberculosum amplicon

<400> SEQUENCE: 27
agcgtatccc gggacccgcg gggattcggt gtagcgggtg tagtcagcgc cgccgccata 60
gtcttgccgg ccgtatgtcg tggcgccttg ctggtagccc tggtcgtaac cgccttggtc 120
ggggtaagcc ggtcgttgct cgggcgggcc cggagggcca gagggcacat agctgccctc 180
ctcgtggcga gccgggccac gcccgtactc cccgtacccg ccgtagccgg gctggccgcc 240
accgggtgaa gggccgtagc cgccgctttg gcgatagccc tggtcgtagc cgggagcgcc 300
gtagccggca gccgggccgg gagaaacagg agggcgttgc tcgtagggcg gcggatagcc 360
cccctgccct tggtcggggt agcctcgacc ctggtcctgg tacccgcgct ggtcggggta 420
gccgcgttgc tcggggtaac cgcgttgctc ggggtaaccg ccctggtcgg ggtacccgat 480
ttgctcgggg tagtcgccct ggtccgggtg gcgcgggcgt gggtagcccg gctggggcgg 540
gtagccgccc gtctcgggtg gatacccccc gcgggggtca gatccgcctt gcggatccgg 600
gccaccacgc ggatcctctt gcggacgcgc atagcggtcg tcgtaatact cgtcgggacg 660
cccctgcccc tgaccgccac ggtagctcga attgtcactc attggtgcta ctcctggttc 720
tgcgccaaac gcgtggtttg attgtggccg ggcgcaatcg atgaccggcg g 771

HIGH RESOLUTION TYPING SYSTEM FOR PATHOGENIC *MYCOBATERIUM TUBERCULOSUM*

CLAIM TO DOMESTIC PRIORITY

This application claims the benefit of priority to U.S. Provisional application Ser. No. 60/397,224 entitled "A High Resolution Typing System For Pathogenic *Mycobacterium tuberculosum*" filed Jul. 19, 2002, by Paul S. Keim et al., and is herein incorporated by reference in its entirety.

FIELD OF THE INVENTION

The present invention is generally directed to sub-typing *Mycobacterium tuberculosum*, the causative agent of tuberculosis, and is more specifically directed to PCR amplification of variable number tandem repeat sequences (VNTR) with primer pairs designed to amplify specifically certain VNTR identified in *Mycobacterium tuberculosum* isolates. Results of the analysis may be compared to results from known *Mycobacterium* species to determine the sub-type of the species for epidemiological and diagnostic purposes.

BACKGROUND OF THE INVENTION

Tuberculosis (TB) is the primary cause of death due to a single microbial pathogen, accounting for 2 to 3 million deaths and an estimated 8 to 10 million new cases per year worldwide (1). It is estimated that one third of the world's population is infected with *Mycobacterium tuberculosum*. The global epidemic is growing, concomitant with HIV co-infection and the increasing prevalence of drug resistant strains. Genotyping clinical isolates of *M tuberculosum* has the potential to significantly impact both clinical practice and public health. Clinically, determining strain relationships can distinguish treatment failure versus potential laboratory cross-contamination, and reactivation of drug-resistant disease versus infection with another strain (24). In the public health arena, determining strain relationships during the course of a tuberculosis outbreak can focus public health resources. However, the most discriminatory *M tuberculosum* genotyping method, IS6110 restriction fragment length polymorphism (RFLP) analysis, is time-consuming, technically demanding, and difficult to standardize between laboratories (3). In addition, IS6110 RFLP does not provide sufficient strain discrimination when fewer than six IS6110-hybridizing bands are present. A secondary genotyping method is required in these instances. A number of PCR-based genotyping methods have been developed, but are limited in their ability to reproducibly provide a level of strain discrimination that matches associations defined by traditional epidemiology. In addition, the high degree of coding region sequence conservation between strains of *M tuberculosum* virtually excludes the use of more commonly used population genetics methods like multi-locus enzyme electrophoresis, restriction fragment length end labeling analysis, and gene sequencing (12).

Spoligotyping is currently the most widely used PCR-based method of *M. tuberculosum* genotyping due to the relative technical ease of the protocol and the ability to compare results between laboratories using a standardized nomenclature system (6). However, the discriminatory power of this method is low. In a database of 3,319 spoligotypes from isolates collected in geographically distinct areas, seven spoligotype patterns were found for 37% of all clustered isolates (18). These spoligotype patterns are associated with strains having a much larger variety of IS6110 RFLP patterns. For instance, 18% of isolates in the spoligotype database had the "Beijing" spoligotype pattern, characterized by the presence of spacer oligonucleotides 39 through 43 (18). However, although the W-Beijing family of strains is recognized as one of the most homogeneous families of *M. tuberculosum* strains (19), the Beijing spoligotype is associated with at least 450 distinct strains as determined by IS6110 RFLP analysis (2).

Following the public release of the complete genomic sequences of *M. tuberculosum* strains H37Rv and CDC-1551, investigators began the process of identifying repetitive genetic elements to develop higher resolution DNA typing systems. Variable number tandem repeats (VNTR) of 21–111 bp genetic elements have been identified (9, 14, 17, 20, 21). A set of 12 VNTRs, also known as mycobacterial interspersed repeat units (MIRUs), was more discriminatory than IS6110 RFLP when used to analyze 180 *M. tuberculosum* isolates with 6 or fewer IS6110-hybridizing bands. The combination of MIRU analysis and spoligotyping and IS6110 RFLP analysis has provided maximum specificity (5).

However, a greater discriminatory power for resolution and differentiation of species is necessary for sub-typing *Mycobacterium tuberculosum* species in order to track sources of infection and ultimately to prevent the spread of disease. Methods and means for determining the genetic differences between *M. tuberculosum* species with speed, accuracy and with great discriminatory capacity have been sought.

SUMMARY OF THE INVENTION

Figure 1:
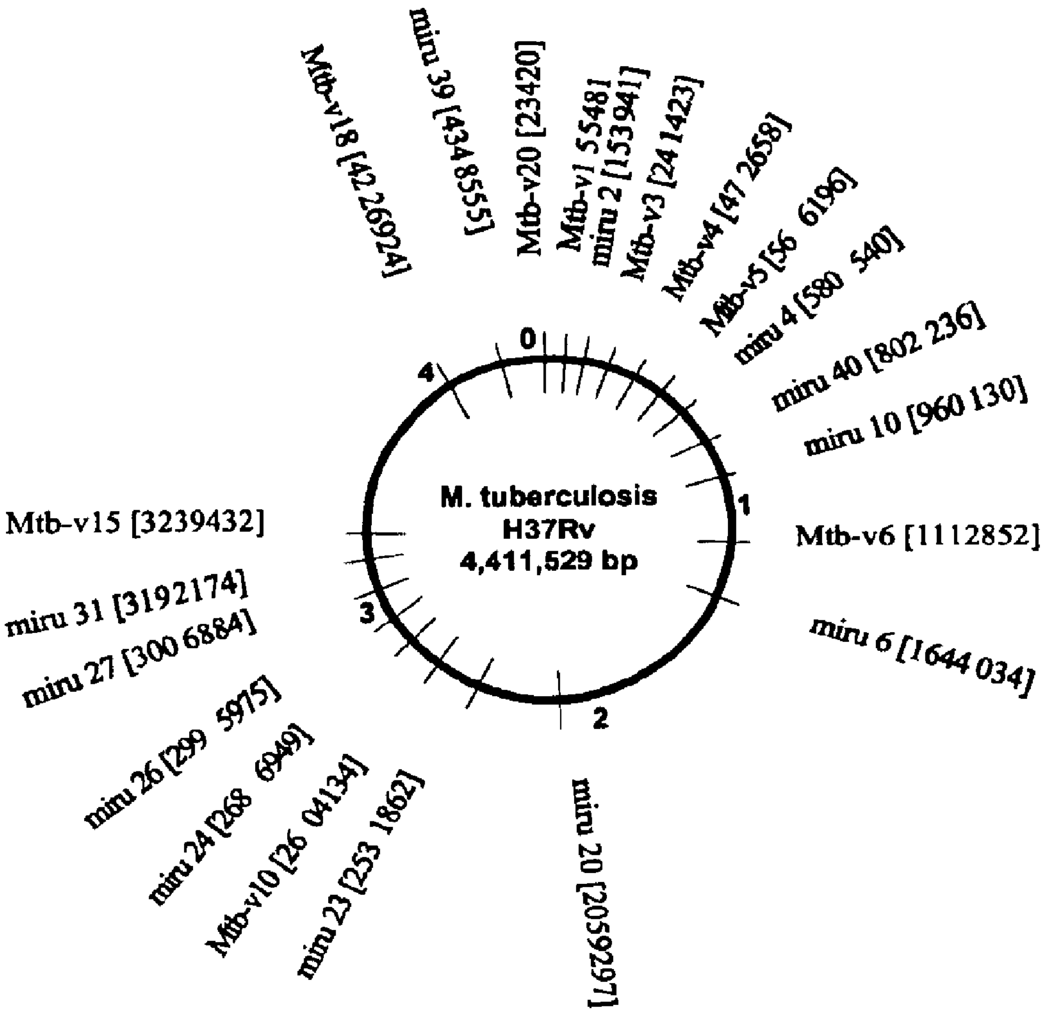
FIG. 1. is a genomic survey location of MLVA and MIRU markers. The location of nine MLVA and 12 MIRU markers are shown on the H37Rv genome. The number in brackets indicates the location of the 5' forward primer for each marker. All accession numbers of forward primer locations are given using the H37Rv sequence.

The present invention discloses methods and means for detecting and sub-typing *M. tuberculosum* species by multi-locus VNTR analysis (MLVA) genotyping system of VNTR identified within the genome of *M. tuberculosum* In the system, independent, tandemly-inserted repeated motifs in the *M. tuberculosum* genome are amplified using fluorescently-labeled primers in multiplexed PCRs and electrophoretically separated on polyacrylamide gels for analysis.

VNTR loci located throughout the H37Rv genome have been identified. Isolated nucleic acids having the sequence of VNTRs identified in *M. tuberculosum* are presented. In an important aspect of the present invention nucleic acids comprising at least 12, 15, 18 or total consecutive nucleotides of a nucleotide sequence selected from the group consisting of SEQ ID NO: 1, SEQ ID NO: 2, SEQ ID NO: 3; SEQ ID NO: 4; SEQ ID NO: 5; SEQ ID NO: 6; SEQ ID NO: 7; SEQ ID NO: 8; SEQ ID NO: 9 SEQ ID NO: 10 SEQ ID NO: 11 SEQ ID NO: 12 SEQ ID NO: 13 SEQ ID NO: 14 SEQ ID NO: 15 SEQ ID NO: 16 SEQ ID NO: 17 and SEQ ID NO: 18 and sequences complementary thereto are presented.

In certain preferred embodiments of the invention, these nucleic acids are immobilized on a solid surface and are useful, for example, in the detection of a *M. tuberculosum* species in an assay employing probes, including, but not limited to, a nano-detection device.

In another important aspect of the invention, primer pairs comprising a forward and a reverse primer are presented for amplification of VNTR located in DNA from a *M. tuberculosum* species. Primer pairs suitable for POR amplification of VNTR, by MLVA or by multiplex, may be selected from the group consisting of SEQ ID NO: 1 and 2, SEQ ID NO: 3 and 4, SEQ ID NO: 5 and 6, SEQ ID NO: 7 and 8, SEQ ID NO: 9 and 10, SEQ ID NO: 11 and 12, SEQ ID NO: 13 and 14, SEQ ID NO: 15 and 16, and SEQ ID NO: 17 and 18. Certain preferred primer pairs have, in addition, an observable group whereby amplified product may be detected. Such groups may be, for example, a fluorescent group or a radioactive group.

In yet another important aspect of the invention, a method for detecting a *M. tuberculosum* species is presented. The method comprises the steps of:

i. obtaining a DNA sample from said species, ii. amplifying a VNTR marker loci in said DNA with one or more primer pairs; and iii. detecting an amplification product that contains the VNTR sequence.

In another important aspect of the invention, MLVA methods are presented for observing polymorphisms at VNTR loci in DNA from more than one *M. tuberculosum* species to resolve unique genotypes between the species and to allow sub-typing of the species into distinct groups. These MLVA methods provide a convenient and rapid method for strain discrimination in *M. tuberculosum*. MLVA may be applied for strain discrimination among globally diverse *M. tuberculosum* isolates.

The method of sub-typing a *M. tuberculosum* strain comprises the steps of:

i. obtaining DNA from said strain;

ii. amplifying said DNA with one or more primer pairs selected from the group consisting of SEQ ID NOS: 1–8 and 9;

iii. detecting said amplified product;

iv. determining the diversity number of said amplified product; and v. comparing said diversity number with the diversity number for a known strain of *M. tuberculosum.*

The method may further comprise MIRU analysis for further discrimination of species.

In yet another important aspect of the invention, kits are provided for detecting and sub-typing *M. tuberculosum* species. The kits comprise one or more primer pairs suitable for amplifying VNTR in DNA in a sample of said species and may comprise, in addition, nucleic acids, enzymes, tag polymerase, for example, and buffers suitable for causing amplification by PCR, by MLVA or by multiplex, for example. In certain preferred embodiments of the kit the primers comprise a label whereby amplified VNTR may be detected. In other preferred embodiments of the kit, labeled nucleic acids are provided. Observable labels are preferably fluorescent molecules or radionucleotides. Certain kits comprise in addition primers and reagents for MIRU analysis of a DNA isolate.

DETAILS OF THE INVENTION

MLVA methods are presented for rapid genotyping of *M. tuberculosum* MLVA targets described herein provide discriminatory power that enhances the ability of present methods to determine rapidly molecular relationships of *M. tuberculosum* isolates. A system comprising a combination of VNTR and MIRU analyses is provided for rapid genotyping of *M. tuberculosum.*

This MLVA typing system is a PCR-based method for genotyping *M. tuberculosum* using VNTR loci identified in the present invention. This PCR-based typing has advantages not present in other PCR-systems: rapid turnaround, amplification with crudely isolated or minute amounts, of DNA, and the ability to use nonviable samples which can be transported across various labs with greater ease than viable ones. The rapid typing system using nine VNTR loci has been used to group a collection of 57 isolates of limited diversity (all had 4 IS6110 bands), and 34 isolates from the Beijing strain family. Smaller repeat motifs, for example <50 bp, as credible additions to the molecular typing of *M. tuberculosum* may also be used. In the MLVA system fluorescent labeling of primer and size of each allele allow for unique and easy identification of each VNTR. Automated gel analysis allows for a high throughput system that reduces error and time in obtaining results. High resolution electrophoresis and discrete repeats allows for the use of standardized data sets and facilitates central databases. An example of the database obtained is given in Table 4.

The ultimate utility of VNTR loci lies in their diversity. The present invention discloses the use of marker diversity using both allele number and frequency to sub-type *Mycobacterium tuberculosum* species. VNTR markers that exhibit high diversity values possess great discriminatory capacity for identifying genetically similar strains. Less diverse markers may be applied with greater utility in species identification and the analysis of evolutionary relationships. This demonstrated ability to predict VNTR diversity based upon array size allows the guided selection of marker loci.

MLVA analysis using the VNTRs presented here can also contribute to the MIRUs recently developed by Mazars et al. (Mazars, E., S. Lesjean, A. L. Banuls, M. Gilbert, V. Vincent, B. Gicquel, M. Tibayrenc, C. Locht, and P. Supply 2001. High-resolution minisatellite-based typing is a portable approach to global analysis of *Mycobacterium tuberculosum* molecular epidemiology as described in Proceedings of the National Academy of Sciences of the United States of America. 98:1901–6)(14), herein incorporated in its entirety. The primers of the present invention may be labeled with the same fluorescent dyes as used in the MIRU set, and may be analyzed on the same electrophoretic run as the MIRUs because of their smaller size and allele composition. MIRU and Mtb markers may be incorporated into the same PCR multiplex reactions. The combination of markers and primers extends the power of the VNTR typing system, without additional time or labor, and increases the discriminatory ability of the present VNTR-typing.

Molecular typing of *M. tuberculosum* using VNTR may produce a useful molecular clock. The "clocking" of a VNTR is a credible methodology for time-geographical correlation In MLVA, different rates of evolution for each VNTR loci may be observed. VNTR markers that match the type of epidemic we are tracking may be chosen. For example, cases of *M. tuberculosum* incidence in endemic areas would intuitively have little variation amongst markers of low diversity. The antithesis of that would be that more diverse markers would be poor for establishing phylogeny across a diverse isolate collection, which is akin to similar findings with IS6110 elements (7). However, with MLVA it is possible to pick and choose what markers would be most appropriate for a given epidemic. For example, it is possible to deduce that VNTR loci with a low diversity index across a worldwide set would have an even lower or non-existent value across a local outbreak. This ability to create a wide gamut of markers of sundry diversity is helpful in a geographically limited area where a particular genetic clone may be more prevalent. The intrinsic value of this concept supports the idea that some VNTR are not suitable for possible transmission routes, but better as informers of plausible evolutionary scenarios, and vice-versa (11, 22).

Some VNTR markers demonstrate an affinity between actual genetic distance and the expansion or contraction of a repeat motif. The dendogram demonstrates this cascading trend with Mtb-v1. Within the Beijing collection, any cluster with a 0.11 difference (one allele) from each other had a repeat motif that differed by only one repeat or allele. For example, MLVA-BJ-A and BJ-B differ by one marker score in Mtb-v10. Yet MLVA-BJ-C and BJ-D, which differ from MLVA-BJ-A and BJ-B by more than one marker allele, have an Mtb-v1 allele size of 110, as opposed to 119 in MLVA-BJ-A and BJ-B. This indicates that phylogeny can be determined further by the difference in repeat motifs of any particular marker. Each marker gives two types of data: the raw score of allele size, and a relative allele relationship. This relative relationship is possible with MLVA, where the diversity within one marker can be greater than 0.5, whereas binary data can give a maximum diversity of 0.5 for any one locus.

The dominance of a particular marker allele could prove a useful tool in quickly referencing a clonal dispersion is a helpful tool in phylogeny studies. The analysis of a distinctive allele type is only viable when multiple loci are combined in analyzing the data. By doing so, it is possible to curtail the effect of convergent evolution in the analysis.

The most immediate public health application of this typing method will be its use during an outbreak. Determination of strain relationship between infected individuals could help in deducing routes of transmission. This information could save time and money for clinics and health-related professionals involved in eradication of *M. tuberculosum*. It is anticipated that this methodology will be a constructive addition to the molecular epidemiological methods currently used to track *M. tuberculosum.*

The following definitions are used herein:

"Polymerase chain reaction" or "PCR" is a technique in which cycles of denaturation, annealing with primer, and extension with DNA polymerase are used to amplify the number of copies of a target DNA sequence by approximately 106 times or more. The polymerase chain reaction process for amplifying nucleic acid is disclosed in U.S. Pat. Nos. 4,683,195 and 4,683,202, which are incorporated herein by reference.

"Primer" is a single-stranded oligonucleotide or DNA fragment which hybridizes with a DNA strand of a locus in such a manner that the 3' terminus of the primer may act as a site of polymerization using a DNA polymerase enzyme.

"Primer pair" is two primers including, primer 1 that hybridizes to a single strand at one end of the DNA sequence to be amplified and primer 2 that hybridizes with the other end on the complementary strand of the DNA sequence to be amplified.

"Primer site" is the area of the target DNA to which a primer hybridizes.

"Multiplexing" is a capability to perform simultaneous, multiple determinations in a single assay process and a process to implement such a capability in a process is a "multiplexed assay." Systems containing several loci are called multiplex systems described, for example, in U.S. Pat. No. 6,479,235 to Schumm, et al., U.S. Pat. No. 6,270,973 to Lewis, et al. and U.S. Pat. No. 6,449,562 to Chandler, et al.

"Isolated nucleic acid" is a nucleic acid which may or may not be identical to that of a naturally occurring nucleic acid. When "isolated nucleic acid" is used to describe a primer, the nucleic acid is not identical to the structure of a naturally occurring nucleic acid spanning at least the length of a gene. The primers herein have been designed to bind to sequences flanking VNTR loci in *Mycobacterium tuberculosum* species. It is to be understood that primer sequences containing insertions or deletions in these disclosed sequences that do not impair the binding of the primers to these flanking sequences are also intended to be incorporated into the present invention.

VNTRs useful in the methods of the present invention for detection and sub-typing *Mycobacterium tuberculosum* have been identified. Eighty-four regions containing tandem repeat sequences as potential VNTRs from the H37Rv sequence were identified. The genomic location of nine identified VNTRs is illustrated in FIG. 1. At least one VNTR marker was discovered in every Mbp region, and five were clustered in the first Mbp. Short sequence repeats (SSRs) that can be readily PCR amplified and molecularly sized with automated fluorescence-based instrumentation were identified.

Table 2 gives the characteristics of these Mtb VNTRs, namely the VNTR loci identification number, amplicon size, size range; motif times repeat and VNTR motif within gene. Table 3 gives the allelic number and diversity of the VNTR across the data set.

TABLE 2

Characteristics of Mtb VNTRs[4].

| VNTR loci | Amplicon size | Size range[1] | Motif × repeat[2] | VNTR motif within gene |
|---|---|---|---|---|
| Mtb-v1 | 113 | 107–119 | 3 × 7 + 1 | PonA - penicillin-resistance gene |
| Mtb-v3 | 152 | 140–152 | 11 × 3 | Rv0203 - hypothetical gene |
| Mtb-v4 | 146 | 137–164 | 9 × 4 + 2 | None - 5' adjacent to Rv0393 |
| Mtb-v5 | 212 | 196–230 | 18 × 3 − 1 | hbhA - Heparin-binding hemagglutin gene |
| Mtb-v6 | 284 | 278–290 | 6 × 4 + 2 | Rv0996 - hypothetical gene |
| Mtb-v10 | 164 | 155–181 | 9 × 3 + 6 | IppP - probable lipo protein-cell wall metabolism |
| Mtb-v15 | 415 | 278–591 | 55 × 2 − 18, 79 × 3 − 133 | None - 5' adjacent to Ribonuclease III gene |

TABLE 2-continued

Characteristics of Mtb VNTRs[4].

| VNTR loci | Amplicon size | Size range[1] | Motif × repeat[2] | VNTR motif within gene |
|---|---|---|---|---|
| Mtb-v18 | 136 | 133–136 | 3 × 4 + 2 | Rv3780 - unknown gene |
| Mtb-v20 | 560 | 560–578 | 18 × 2 + 4 | Rv0019c - conserved hypothetical gene |

[1]Size range given corresponds to range seen across all collections
[2]Numbers with a + or − sign in front represent the number of addition nucleotides present/absent in a complete repeat
[3]Non-tandem polymorphic repeats include: (8 × 6, and 12 × 2)
[4]All table data is collected and representative of findings from the H37Rv strain.

TABLE 3

Allelic number and diversity of VNTR across data set.

| VNTR name | Number of Alleles | Diversity All | Diversity Beijing | Diversity Four-band IS6110 |
|---|---|---|---|---|
| Mtb-v1 | 5 | 0.59 | 0.25 | 0.23 |
| Mtb-v3 | 2 | 0.06 | 0.0 | 0.09 |
| Mtb-v4 | 2 | 0.08 | 0.16 | 0.03 |
| Mtb-v5 | 2 | 0.02 | 0.0 | 0.03 |
| Mtb-v6 | 2 | 0.02 | 0.0 | 0.03 |
| Mtb-v10 | 4 | 0.48 | 0.16 | 0.30 |
| Mtb-v15 | 4 | 0.14 | 0.20 | 0.06 |
| Mtb-v18 | 2 | 0.12 | 0.20 | 0.03 |
| Mtb-v20 | 2 | 0.02 | 0.06 | 0.0 |

Figure 2:
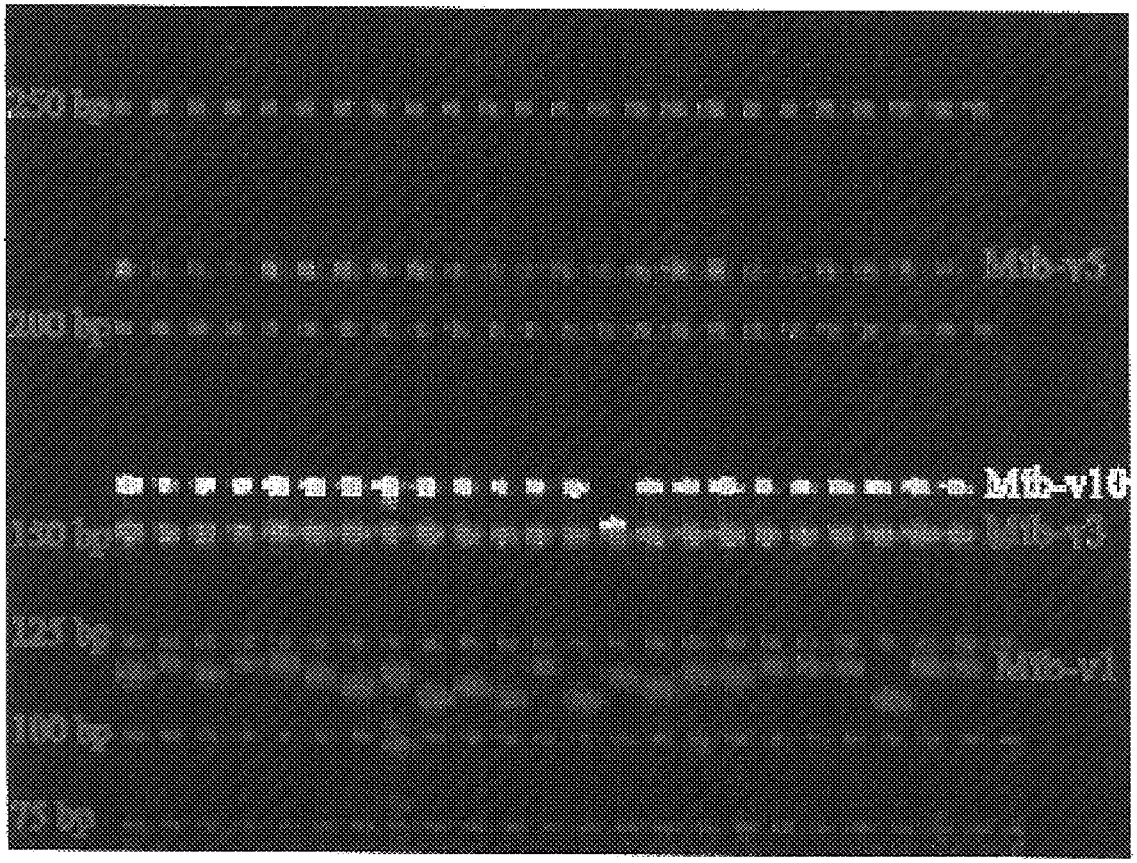
FIG. 2 is a picture of the gel pattern from electrophoresis of MLVA fragments illustrating the fluorescent image of markers Mtb-v1,-v3,-v5, and -v 10 on an ABI377 electrophoresis gel. Each marker allele is identified through a unique size and color combination, allowing adequate discrepant ability across comparable-sized fragments from sundry alleles.

The results of PCR assay of these repeats after electrophoretic separation is given in FIG. 2.

In this relatively homogenous set, diversity across the nine loci varied greatly, as measured by allele number range and diversity value range (Table 3). Six of the loci (Mtb-v1, v3, v5, v6, v10, v15) were variable across the collection of isolates having 4 IS6110 bands, and six loci (Mtb-v1, v4, v10, v15, v18, v20) were variable across the Beijing collection. In contrast, three VNTR loci (Mtb-v1, v10, v15) had four alleles and diversity values ranging from 0.14 to 0.59 across all samples.

As observed in Table 3, a larger number of alleles did not always correspond to a greater diversity value. In one sense, allele number represents potential discrimination power while the diversity value represents the realized discrimination in a given set of samples. Both values are useful for understanding the genetic loci and the isolate sets being observed.

When the 34 Beijing family strains were considered separately, the number of alleles and diversity values dropped. Six marker loci were informative within Beijing strains and three (Mtb-v1, v15, v18) were still relatively diverse, with diversity values of 0.25, 0.20, and 0.20, respectively. Markers Mtb-v4, v15, and were more diverse across the Beijing collection than across the four-bander set (Table. 3). Diversity values for collection of isolates having 4 IS6110 bands ranged from 0.0 to 0.3. The diversity values for Mtb-v5, v6, and v20 correspond to only one allele variation, in one isolate, across the entire collection set as illustrated in Table 4.

The diversity values of Mtb-v1, and Mtb-v1 across the combined strain set were greater than for either strain set alone. This was due to differential allele frequency, as opposed to unique allele number, across each data set. The Mtb-v1 size of 116 bp had a frequency of 88% within the set of strains having four IS6110 bands. In contrast, the allele size of 116 bp was seen on one occasion across the Beijing strain set, a 2.9% frequency. For Mtb-v10, a similar pattern of allele biasness can be seen. The allele size of 154 bp is seen in 84% of the isolates having 4 IS6110 bands. In contrast, the allele size of 154 is not present at all in the Beijing strains. Twenty-nine (85%) of the Beijing strains had an allele size of 163, whereas eight (14%) of the isolates having 4 IS6110 bands had an allele size 163. Hence the higher diversity value across Mtb-v1 and Mtb-v10 when the data is combined.

The present invention provides primer pairs for PCR amplification of VNTR in DNA of *M. tuberculosum*. The primer pairs comprise a forward primer and a reverse primer. Table 1 illustrates the *M. tuberculosum* Primer Sequences of the present invention. Table 1 also gives the source (location) of the VNTR. The location of each VNTR locus is given by the 5' of the forward primer in accordance with the H37Rv reference strain.

TABLE 1

Name, Location, and sequence of primers

| Primer | Location (kb)[a] | Forward Primer Sequence | Reverse Primer Sequence |
|---|---|---|---|
| Mtb-v1 | 55,481 | GTCGAACGAGACTTTCCCCAAACCGAC | GACCGTGGGCTGGATGACGGTCTC |
| Mtb-v3 | 241,423 | GATGACGGATCGTCGGGGGCGGGAAC | GCAACGCGAGGGCGATCAGTACTGCCAACA |
| Mtb-v4 | 472,658 | GCTGTGGCGCAGCTACACAGTACGACTC | GATTGCGCAGCGCCCAACAGC |
| Mtb-v5 | 566,196 | GGAGGCGTTGGGTACGGTCGCATC | GATTCGGAGCCCGACTACTTCTGGGT |
| Mtb-v6 | 1,122,852 | CGCCGACGAGGCCGATGCCGAAGC | CCGCGGCGGCAGAGCCAACCAGGAT |
| Mtb-v10 | 2,604,134 | CGAGGCGCCCAGCCCCACAA | CACCCGCGCTTTAGGATCGACACCTGA |
| Mtb-v15[b] | 3,239,432 | GCGCCGCACCACCTCGACTT | CCGGGCAAAACCTCCGCCTAAC |

TABLE 1-continued

| Name, Location, and sequence of primers | | | |
|---|---|---|---|
| Primer | Location (kb)[a] | Forward Primer Sequence | Reverse Primer Sequence |
| Mtb-v18 | 4,226,924 | ACAACGGCGAGGCCCGAATCTACGAA | GTCGACGCCGCCGATGACC |
| Mtb-v20[c] | 23,420 | CCCGGAGGGCCAGAGGGCACATAGC | TGGCGCAGAACCAGGAGTAGCACCAATGAG |

[a]Location of VNTR locus is given by the 5' of the forward primer in accordance with the H37Rv reference strain sequenced in 1998.
[b]Mtb-v15 is designed loci ETR-F, named and developed by Frothingham, and its similar location was identified retrospectively here (9).
[c]Mtb-v20 was recently identified by Le Fleche(13), and given the name Mtub01.

These primer sequences have herein been assigned SEQ ID NO: as follows:

TABLE 4

| SEQ ID NO | Marker Name | Primer Type |
|---|---|---|
| SEQ ID NO: 1 | Mtb-v1 | Forward primer |
| SEQ ID NO: 2 | Mtb-v1 | Reverse primer |
| SEQ ID NO: 3 | Mtb-v3 | Forward primer |
| SEQ ID NO: 4 | Mtb-v3 | Reverse primer |
| SEQ ID NO: 5 | Mtb-v4 | Forward primer |
| SEQ ID NO: 6 | Mtb-v4 | Reverse primer |
| SEQ ID NO: 7 | Mtb-v5 | Forward primer |
| SEQ ID NO: 8 | Mtb-v5 | Reverse primer |
| SEQ ID NO: 9 | Mtb-v6 | Forward primer |
| SEQ ID NO: 10 | Mtb-v6 | Reverse primer |
| SEQ ID NO: 11 | Mtb-v10 | Forward primer |
| SEQ ID NO: 12 | Mtb-v10 | Reverse primer |
| SEQ ID NO: 13 | Mtb-v15 | Forward primer |
| SEQ ID NO: 14 | Mtb-v15 | Reverse primer |
| SEQ ID NO: 15 | Mtb-v18 | Forward primer |
| SEQ ID NO: 16 | Mtb-v18 | Reverse primer |
| SEQ ID NO: 17 | Mtb-v20 | Forward primer |
| SEQ ID NO: 18 | Mtb-v20 | Reverse primer |

The polynucleotides of the present invention may be prepared by two general methods: (1) they may be synthesized from appropriate nucleotide triphosphates, or (2) they may be isolated from biological sources. Both methods utilize protocols well known in the art. The availability of nucleotide sequence information enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector Methods for using these primer pairs to amplify VNTR loci in *Mycobacterium tuberculosum* are disclosed herein. Generally MLVA analyses or multiplex systems known to the art may be employed to detect and sub-types *Mycobacterium tuberculosum*. PCR instruments, for example, thermo-cyclers, used in these amplification methods are commercially available.

Figure 3:
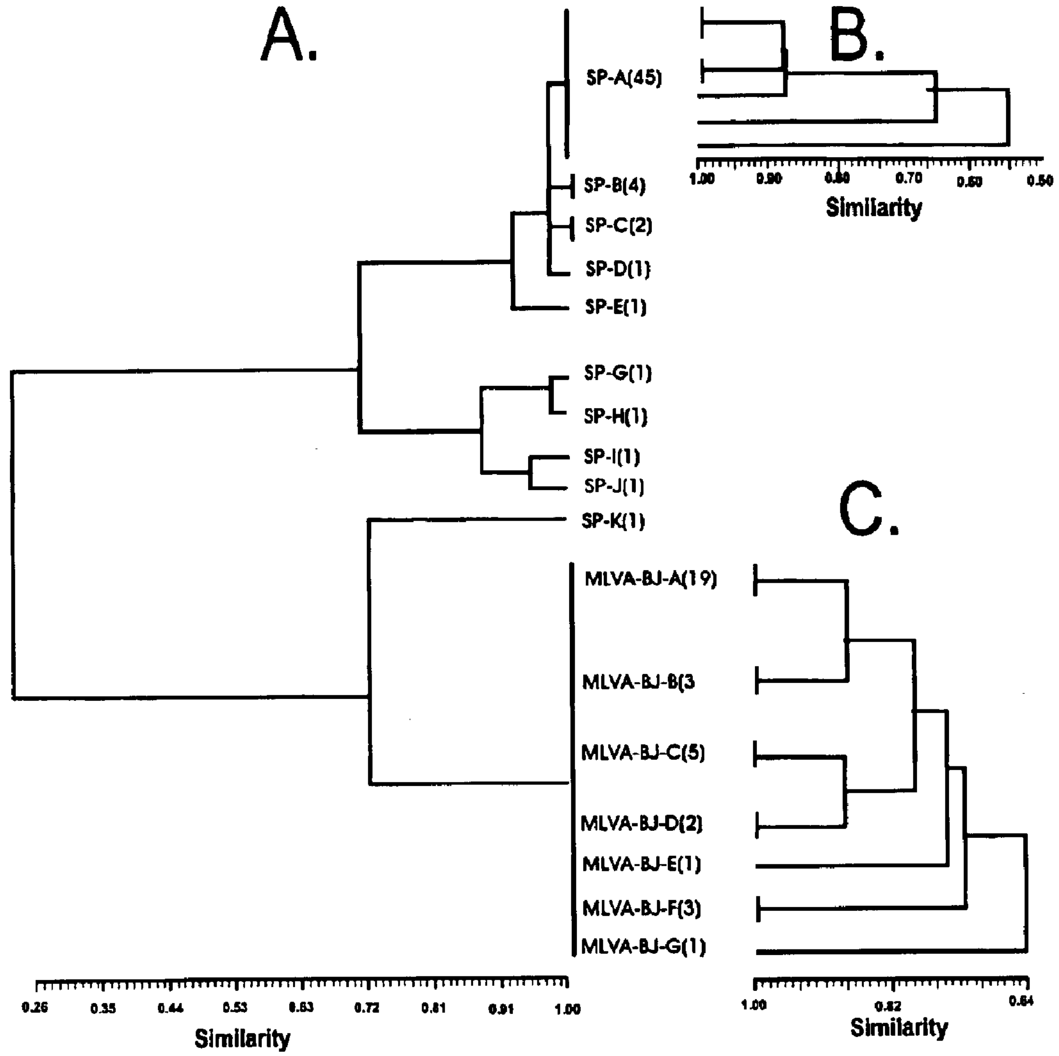
FIG. 3. is a dendrogram illustrating grouping resulting from UPGMA analysis of spoligotyping (A) and MLVA (B, C) data. Clustering using spoligotyping data across 91 isolates is shown (A). The group SP-A is broken into five genotypes using MLVA (B). For section C, MLVA resolves the Beijing cluster into seven genotypes, designated MLVA-BJ-A through BJ-G.

Methods for applying MLVA of these VNTR for strain discrimination among *M. tuberculosum* isolates are disclosed. Polymorphisms at these loci were may be used to resolve genotypes into distinct groups. Among all 91 isolates, the nine-marker MLVA identified 17 unique genotypes. 12 unique MLVA genotypes are shown in FIG. 3, which were identified from 2 spoligotype clusters, Sp-A, and Sp-L. Spoligotype genotype cluster A was represented by five MLVA genotypes (FIG. 3*b*.). While the Beijing family isolates (34 total), were subdivided into seven unique types (FIG. 3*c*) based upon six informative marker loci (Table 2). Two of the isolates were unique, with the other isolates in clusters of 19, 5, 3, 3, and 2 (FIG. 3*c*).

As observed in Table 3, a larger number of alleles did not always correspond to a greater diversity value. In one sense, allele number represents potential discrimination power while the diversity value represents the realized discrimination in a given set of samples. Both values are useful for understanding the genetic loci in any isolate being observed.

The amplicon size range for 7 of the loci is 107–290 bp. This size range allows for electrophoresis runs of roughly 2 hours on the ABI377 system (Applied Biosystems Incorporated, Foster City, Calif.). Two markers (Mtb-v15, Mtbv-20) have larger ranges from 278–591 bp (Table. 2). The number of alleles across these nine loci ranged from 2 to 8 (Table 3).

All of the polymorphic markers, except Mtb-v20, contained three or more copies of a tandem repeat sequence in the H37Rv sequence. Of these, seven had repeat motifs of three base multiples (Table 2), consistent with “in-frame” insertion and deletion mutational events. Seven loci were within hypothetical or known ORFs, while two were adjacent to genes (Table 2).

FIG. 3 is a dendogram based upon Unweighted Pair Group Method Arithmetric Average (UPGMA) analysis of spoligotyping (A) and MLVA (B, C) data. illustrating the resolution of unique genotypes into distinct groups. Clustering using spoligotyping data across all 91 isolates is shown (A). The group SP-A is broken into five genotypes using MLVA (B). For section C, MLVA resolves the Beijing cluster into seven genotypes, designated MLVA-BJ-A through BJ-G.

The present MLVA methods provide high species discrimination and sub-typing of *Mycobacterium tuberculosum*. Spoligotyping differentiated the 91 isolates into nine unique genotypes (FIG. 3*a*). The spoligotyping dendogram revealed the deepest branch at 0.26, which would concur with the number of loci considered in UPGMA, which is 43. By definition, the Beijing strains share spoligotype pattern designation 000000000003771 (6).

In addition IS6110-based restriction fragment length polymorphism (RFLP) may be used in a sub-typing scheme.

TABLE 5

Clustering defined by IS6110 RFLP, spoligotype, and VNTR analyses[±].

| Cl. | n | Dsg. | IS6110 Pattern | Spoligotype | v1 | v3 | v4 | v5 | v6 | v10 | v15 | v18 | v20 |
|---|---|---|---|---|---|---|---|---|---|---|---|---|---|
| 1 | 1 | 4.001 | 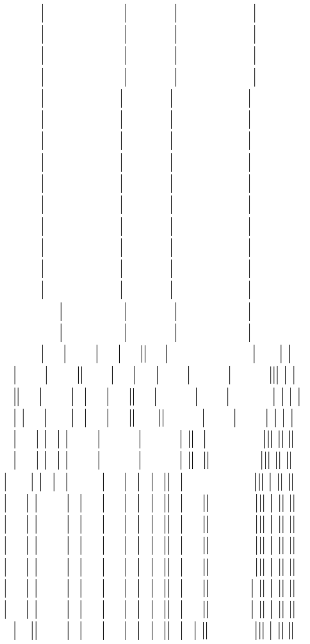 | 777776777760771 | 110 | 152 | 146 | 214 | 278 | 163 | 400 | 136 | 561 |
| 2 | 1 | 4.001 | | 777776777760771 | 116 | 152 | 146 | 214 | 284 | 154 | 348 | 136 | 561 |
| 3 | 25 | 4.001 | | 777776777760771 | 116 | 152 | 146 | 214 | 284 | 154 | 400 | 136 | 561 |
| 4 | 3 | 4.001 | | 777736777760771 | 116 | 152 | 146 | 214 | 284 | 154 | 400 | 136 | 561 |
| 5 | 1 | 4.002 | | 777777777760771 | 116 | 152 | 146 | 214 | 284 | 154 | 400 | 136 | 561 |
| 6 | 1 | 4.002 | | 777776777760771 | 113 | 140 | 146 | 214 | 284 | 163 | 455 | 136 | 561 |
| 7 | 1 | 4.002 | | 777776777760771 | 113 | 152 | 146 | 198 | 284 | 172 | 400 | 136 | 561 |
| 8 | 2 | 4.002 | | 777776777760771 | 113 | 152 | 146 | 214 | 284 | 154 | 400 | 136 | 561 |
| 9 | 14 | 4.002 | | 777776777760771 | 116 | 152 | 146 | 214 | 284 | 154 | 400 | 136 | 561 |
| 10 | 2 | 4.002 | | 700076777760771 | 113 | 152 | 146 | 214 | 284 | 163 | 400 | 136 | 561 |
| 11 | 1 | 4.002 | | 700076777760771 | 116 | 152 | 146 | 214 | 284 | 163 | 400 | 136 | 561 |
| 12 | 1 | 4.002 | | 777736777760771 | 116 | 152 | 146 | 214 | 284 | 154 | 400 | 136 | 561 |
| 13 | 1 | 4.002 | | 000000377760771 | 116 | 152 | 146 | 214 | 284 | 163 | 400 | 136 | 561 |
| 14 | 1 | 4.002 | | 771776777660771 | 116 | 152 | 146 | 214 | 284 | 154 | 400 | 136 | 561 |
| 15 | 1 | 4.008 | | 700076777760700 | 116 | 140 | 146 | 214 | 284 | 163 | 400 | 136 | 561 |
| 16 | 1 | 4.008 | | 700076717760700 | 116 | 152 | 146 | 214 | 284 | 163 | 400 | 136 | 561 |
| 17 | 3 | 10.012 | | 000000000003771 | 119 | 152 | 146 | 214 | 284 | 181 | 348 | 136 | 561 |
| 18 | 4 | 15.024 | | 000000000003771 | 119 | 152 | 146 | 214 | 284 | 163 | 400 | 136 | 561 |
| 19 | 2 | 16.003 | | 000000000003771 | 119 | 152 | 146 | 214 | 284 | 163 | 400 | 136 | 561 |
| 20 | 1 | 16.003 | | 000000000003771 | 119 | 152 | 146 | 214 | 284 | 163 | 400 | 136 | 561 |
| 21 | 1 | 17.001 | | 000000000003771 | 119 | 152 | 155 | 214 | 284 | 163 | 400 | 136 | 561 |
| 22 | 1 | 17.001 | | 000000000003771 | 119 | 152 | 155 | 214 | 284 | 163 | 400 | 136 | 561 |
| 23 | 1 | 18.010 | | 000000000003771 | 119 | 152 | 155 | 214 | 284 | 163 | 400 | 136 | 561 |
| 24 | 1 | 21.001 | | 000000000003771 | 107 | 152 | 146 | 214 | 284 | 163 | 348 | 136 | 579 |
| 25 | 2 | 21.001 | | 000000000003771 | 110 | 152 | 146 | 214 | 284 | 163 | 400 | 133 | 561 |
| 26 | 1 | 21.001 | | 000000000003771 | 116 | 152 | 146 | 214 | 284 | 163 | 319 | 136 | 561 |
| 27 | 4 | 21.001 | | 000000000003771 | 119 | 152 | 146 | 214 | 284 | 163 | 400 | 136 | 561 |
| 28 | 5 | 21.001 | | 000000000003771 | 110 | 152 | 146 | 214 | 284 | 163 | 400 | 133 | 561 |
| 29 | 3 | 21.001 | | 000000000003771 | 119 | 152 | 146 | 214 | 284 | 163 | 400 | 136 | 561 |
| 30 | 5 | 21.001 | | 000000000003771 | 119 | 152 | 146 | 214 | 284 | 163 | 400 | 136 | 561 |

[±]Where cluster (Cl.) designates a group of isolates with a distinct genotype defined by IS6110 RFLP, spoligotype, and multi-locus VNTR analysis; n is the number of isolates within the cluster; the IS6110 RFLP is numerically designated (Dsg.) and the image is shown with high to low molecular weights oriented from left to right; spoligotype nomenclature as defined by Date, 2001 (6); and Mtb-v1 through Mtb-v20 indicate the amplicon size (number of base pairs) observed for the corresponding VNTR amplicons.

The system of analysis has been applied to the globally prevalent homogeneous W-Beijing family of strains. Two sets of clinical isolates of *M. tuberculosum*: a set of 34 Beijing strains and another set of 57 isolates having 4 IS6110 RFLP bands. The details of this analysis are presented in the Experimental Section hereinbelow The results of these analyses illustrate that the characterization of molecular diversity with MLVA to the strain-typing of *Mycobacterium tuberculosum* method can be used for the rapid discrimination and identification of remaining major *Mycobacterium tuberculosum* species. They also illustrate that the sub-typing scheme useful for the epidemiological study of *Mycobacterium tuberculosum* may be applied to the local detection of the pathological causative agent of tuberculosis.

Kits are herein provided for use with commercially available PCR instruments to detect and sub-type strains of *Mycobacterium tuberculosum*. The kits contain one or more primer pairs disclosed hereinabove having SEQ ID NOS: 1–18 for amplifying the VNTR in DNA isolated from a *Mycobacterium tuberculosum* sample. If the sample is to be multiplexed, the kits may contain a suitable "cocktail" of primer pairs.

The kits may also contain nucleic acids needed in the amplification process. The nucleic acids may be tagged by a suitable marker, a fluorescent probe or a radioactive molecule. Any tag for marking the nucleic acid after amplification and size separation as by electrophoresis or other separation means is suitable. In certain preferred embodiments of the invention, the primer pairs themselves comprise a suitable marker.

The kits may also comprise enzymes, taq polymerase, for example and salts and buffers suitable for causing amplification of DNA by PCR. This kits may also comprise suitable containers and bottles for housing these reagents and or convenient use.

Kits for sub-typing strains of *Mycobacterium tuberculosum* comprise, in addition, DNA isolated from known *Mycobacterium tuberculosum* strains. This isolated DNA containing VNTR loci may be used as standards in the sub-typing of the species. In certain instances the kits may comprise in addition primers and standard references for MIRU analysis.

EXPERIMENTAL SECTION

The following experiments illustrate the materials and methods used in genotyping *M. tuberculosum* isolates by MVLA with the primers of the present invention.

Source of *Mycobacterium tuberculosum* Strains.

As part of the Centers for Disease Control and Prevention (CDC) National Tuberculosum Genotyping and Surveillance Network, the University of Texas Health Science Center at San Antonio (UTHSCSA) serves as a genotyping reference laboratory for *M. tuberculosum* isolates collected by the Texas Department of Health (TDH). From 1996 to present, isolates from 4,269 persons with TB were genotyped (4, 15). The Institutional Review Boards of the TDH and the UTHSCSA approved culture collection and analyses (TDH-CDC cooperative agreement, TDH protocol number 980025, and UTHSCSA protocol number 001-6000-105). Two sets of clinical isolates were analyzed. One set consisted of 57 isolates having four IS6110 RFLP bands. The second set included 34 isolates with an identical Beijing spoligotype pattern containing spacer oligonucleotides 36–43 and 14 different IS6110 RFLP patterns.

DNA Isolation

*M. tuberculosum* isolates were grown on Lowenstein-Jensen media slants (Becton, Dickinson, and Co., Franklin Lakes, N.J.) for four to six weeks at 37° C. under 5% $CO_2$. In a BioSafety Level 3 facility, the bacterial mass was removed using a sterile inoculating loop, placed in a microcentrifuge tube containing 1 ml $ddH_2O$, and heat-killed at 85° C. for 20 min. The cells were pelleted by centrifugation and resuspended in a 10 mM Tris-HCl, 1 mM EDTA buffer (pH 8.0). Cell walls were digested with lysozyme (10 mg/ml), proteinase K (10 mg/ml), and 10% sodium dodecyl sulfate. DNA was extracted using 0.3 M cetyltrimethylammonium bromide and 5M NaCl, purified by chloroformisoamyl alcohol separation, and precipitated using isopropanol (Sigma, St. Louis, Mo.).

Spoligotyping

Spoligotype analyses (10) were done using locally synthesized and biotinylated PCR primers (UTHSCSA Advanced Nucleic Acids Technology Core Facility, San Antonio, Tex.) and commercially available spoligotyping membranes (Isogen, Maarssen, The Netherlands) as previously described (15).

IS6110 RFLP Analysis.

IS6110-based restriction fragment length polymorphism (RFLP) was performed by Southern blotting of PvuII-digested genomic DNA using a 523 bp (base pair) right-handed IS6110 probe (23), the ECL™ detection system (Amersham, Piscataway, N.J.), and BioImage Whole Band Analyzer version 3.4.2 (Genomic Solutions, Ann Arbor, Mich.) as previously described (15).

VNTR Identification and Primer Design

The complete genome sequence of the *Mycobacterium tuberculosum* H37Rv strain was downloaded from the Sanger Centre website. Potentially polymorphic repetitive sequences were identified using the DNAstar software program Genequest (Lasergene, Inc Madison, Wis.). Selection criteria of repetitive sequence were set for nucleotide repeat motifs of more than 8 bp within 100 bp proximity of each other. Primers were designed around 84 repetitive sequences identified using the DNAstar software program Primer Select (Lasergene, Inc Madison, Wash.). Complementary primers were designed around interspersed repeats to minimize risk of mobile DNA targets. Fifteen of these repetitive sequences were found to be polymorphic, i.e., VNTR loci. Nine loci were chosen for use in these analyses (Table. 1).

PCR Amplification of VNTR Loci

PCR reactions were performed using a total volume of 10 μL. All PCR reagents used were obtained from In Vitrogen (Madison, Wis.) unless otherwise indicated. Each PCR reaction mix contained the following reagents and concentrations: 1×PCR buffer (20 mM Tris-HCL [pH 8.4], 50 mM KCL); 2 mM $MgCl_2$, 200 uM of each four deoxynucleoside triphosphates (dNTPs), 0.4 Units of Platinum Taq Polymerase (Gibco-Life Technologies) per uL, 0.2 uM forward primer, 0.2 uM reverse primer R110, R6G, or Tamara phosphoramide fluorescent labeled oligonucleotides (Perkin Elmer Biosystems), 1 uL DNA template, and $ddH_2O$ bringing the total volume to 10 uL. Each 10 μl PCR mix was then denatured for 5 minutes at 95° C. Following the denaturing, the samples were cycled 35 times through the following program: 95° C. for 20 seconds, 55° C. for 25 seconds, and 72° C. for 20 seconds. These 35 cycles were followed by a final extension at 72° C. for 5 minutes and the samples were then stored at −20° C. until genotyped. Reactions that failed under the above conditions were then repeated with 2 ul of DNA in a 10 ul reaction; all other concentrations and conditions remaining the same.

Genotyping

Detailed automated genotyping methods have been described previously (Keim, P., L. B. Price, A. M. Klevytska, K. L. Smith, J. M. Schupp, R. Okinaka, P. J. Jackson, and M. E. Hugh-Jones. 2000. Multiple-locus variable-number tandem repeat analysis reveals genetic relationships within *Bacillus anthracis*. Journal of Bacteriology. 182:2928–36)., herein incorporated in its entirety. Briefly, fluorescent labeled amplicons were sized and scored using the ABI software program Genotyper.

Statistical Analysis

Genetic distances were determined by calculating the percentage shared alleles pair-wise among all isolates. The clustering method used was unweighted pair group method arithmetic average (UPGMA). UPGMA clustering analysis was performed using the software program NTSYS (16). There was no missing data across the nine VNTR loci and 91 isolates. The diversity index of each VNTR marker was calculated using $[1-\Sigma(\text{allele frequencies})^2]$ (25).

EXAMPLE 1

This example illustrates the amplicon produced during the amplification of VNTR locus Mtb-v1 with primer pairs SEQ ID NO: 1 and SEQ ID NO: 2.

5' Beginning location of VNTR: 55,533. (All accession numbers are according to the H37Rv *M. tuberculosum* sequence done by the Sanger Institute.

(SEQ ID NO: 19)

GGCTCGGGCCTGCCGTCGGACATCTGGAAGGCAACCATGGACGGCGCC

TTGAAGGGCACGTCGAACGAGACTTTCCCCAAACCGACCGAGGTCGGTGG

TTATGCCGGTGTGCCGCCGCCGCCGCCGCCGCCGGAGGTACCACCTTCG

CAGACCGTCATCCAGCCCACGGTCGAAATTGCGCCGGGGATTACCATCCC

GATCGGTCCCCCGACCACCATTACCCTGGCGCCACCGCCCCCGGCCCCGC

CCGCTGCGACTCCCACGCCGCCGCCGTGACCGGCGCGCTGTCCCAAAGCA

GCAACATCTCGCCACTTCCTTTGGCCGCCGATCTGCGGAGCGCCGATAAC

CGCGATTGCCCCAGCCGCACCGACGTATTGGG

FORWARD PRIMER 5' GTCGAACGAGACTTTCCCCAAACCGAC 3'

REVERSE PRIMER 5' GACCGTGGGCTGGATGACGGTCTC 3'

EXAMPLE 2

This example illustrates the amplicon produced during the amplification of VNTR locus Mtb-v3 with primer pairs SEQ ID NO: 3 and SEQ ID NO: 4.

5' Beginning location of VNTR 241,464. (All accession numbers are according to the H37Rv *M. tuberculosum sequence done by the Sanger Institute.*

(SEQ ID NO: 20)

5'GCGAGCCTACCGAAGATCGCGTGCATGCGTTCGGCGTGGACCGCACAG

CACCTGGAGTTGGCGGCGCCGAGGGCCGAGATGGCAGGATGACCGATCG

TCGGGGGCGGGAACTCCCAGGCCGCCGGGCCGTCGCAAACCCGTCGCAAA

CCCGTCGCAAACCGTAAGGAGTCATCCATGAAGACAGGCACCGCGACGAC

GCGGCGCAGGCTGTTGGCAGTACTGATCGCCCTCGCGTTGCCGGGGGCCG

-continued

CCGTTGCGCTGCTGGCCGAACCATCAGCGACCGGCGCGTCGGACCC,GTGC

GCGGCCAGCGAAGTGGCGAGGACGGTCGGTTCGGTCGCCAAGTCGATGGG

CGACT3'

FORWARD PRIMER 5' GATGACGGATCGTCGGGGGCGGGAAC 3'

REVERSE PRIMER 5' GCAACGCGAGGGCGATCAGTACTGCCAACA 3'

EXAMPLE 3

This example illustrates the amplicon produced during the amplification of VNTR locus Mtb-v4 with primer pairs SEQ ID NO: 5 and SEQ ID NO: 6.

5' Beginning location of VNTR -241,464. (All accession numbers are according to the H37Rv *M. tuberculosum* sequence done by the Sanger Institute.

(SEQ ID NO: 21)

ATTCAGGCCGCCGAATCCACTACCGATGATGACCACGCGATGGCGCCCGC

CGACGGCCGAGGGTTCACCAGATGAGAGCGTCATGGTCCTCCTTCAGTCT

GGTCGCTGTGGCGCAGCTACACAGTACGACTCCCGTCATGCCAACGGCGT

AACTTTTTGTGGGCCTTGTGGGCCTTGTGGGCCTTGTGGGCCTTTGTCGG

GCCGCCTTCGGATCGGACGCTCGGGATGGCTGTTGGGCGCTGCGCAATCC

CGCGCTTCGATCAGGCAGCGTCCGGCAGTGCCATCAATGGCGGCCAGGTA

CACCTCTCCGACGGCTCGACATCGCCGGCCCGGCAGTTACCTGCACCATG

GCCGGGCGATGCGGGAGCGGCTGCCGAAGGTCGGGCAGGTGTTTGCTGCC

GGGGAAATCGACTACCACATGTTTCAGACGTTGGTGTATCGCACCGATTT

GATCACCGACCCGCAGGTGTTGGCGCGGGTGGATGCCGAGCTGGCGCTGC

GGGTGCGGGGCT

FORWARD PRIMER 5' GCTGTGGCGCAGCTACACAGTACGACTC 3'

REVERSE PRIMER 5' GATTGCGCAGCGCCCAACAGC 3'

EXAMPLE 4

This example illustrates the amplicon produced during the amplification of VNTR locus Mtb-v5 with primer pairs SEQ ID NO: 7 and SEQ ID NO: 8.

5' Beginning location of VNTR 241,464. (All accession numbers are according to the H37Rv *M. tuberculosum* sequence done by the Sanger Institute.

(SEQ ID NO: 22)

AGCCAGCAGAGCTTCGAGGAAGTGTCGGCGCGCGCCGAAGGCTACGTGG

ACCAGGCGGTGGAGTTGACCCAGGAGGCGTI'GGGTACGGTCGCATCGCAG

ACCCGCGCGGTCGGTGAGCGTGCCGCCAAGCTGGTCGGCATCGAGCTGCC

TAAGAAGGCTGCTCCGGCCAAGAAGGCCGCTCCGGCCAAGAAGGCCGCTC

CGGCCAAGAAGGCGGCGGCCAAGAAGGCGCCCGCGAAGAAGGCGGCGGC

CAAGAAGGTCACCCAGAAGTAGTCGGGCTCCGAATCACCATCGACTCCGA

GTCGCCCACGGGGCGACTCGGAGTCGACGTGTTGGATGCAAACCGCATAG

TCTGAATGCGTGAGCCACCTCGTGGGTACCGTCATGCTGGTATTGCTGGT

CGCCGTCTTGGTGACAGCGGTGTACGCGTTTGTGCATGCTGCGTTGCAGC

-continued

GGCCCGATGCCTATACCGCCGCCGACAA

FORWARD PRIMER 5' GGAGGCGTTGGGTACGGTCGCATC 3'

REVERSE PRIMER 5' GATTCGGAGCCCGACTACTTCTGGGTGAC 3'

EXAMPLE 5

This example illustrates the amplicon produced during the amplification of VNTR locus Mtb-v6 with primer pairs SEQ ID NO: 9 and SEQ ID NO: 10.

5' Beginning location of VNTR 1,112,923. (All accession numbers are according to the H37Rv *M. tuberculosum* sequence done by the Sanger Institute.

(SEQ ID NO: 23)

GCAGACCGCAGGTGCCGACGAGCCGGACTACTTAGACGTCGATGTGGTC

GAAGAAGACTCGGAGGCGCTTCCGGTGGGGGCTGGCGCTGCGGTCGGCGA

GTCCGCCGACGAGGCCGATGCCGAAGCTGCTGACGGAGTTGCGGGCCACG

CCGACCCGGAGGCCGACCCGGTCGAATACGAATACGAATACGAATACGTC

GAGGACACCTGCGGTTTGGAGCTCGAGGAGGACGACCAGGAAGCGCCACC

GACCGTCGCATCCGGCACGTCACGGCGGCGCCGATTCGACACCAAGACCG

CCGCCGCGGTCAGCGCCCGCAAGTACACCTTCCGCAAACGTGCGTTGATC

GTGATGGCGGTGATCCTGGTTGGCTCTGCCGCCGCGGCCTTCGAGCTGAC

CCCGGTCGCGTGGTGGATCTGTGGTAGCGCCACCGGTGTGACGGTGCTCT

ACCTGGCATATTTGCGTCGGCAAACCCGCATCGAGGAGAAGGTGCGTCGG

CGGCGGATGCAGCGGATCGCGCGGGCGCGGCTCGGTGTAGAGAACACCCG

TG

FORWARD PRIMER 5' CGCCGACGAGGCCGATGCCGAAGC 3'

REVERSE PRIMER 5' CCGCGGCGGCAGAGCCAACCAGGAT 3'

EXAMPLE 6

This example illustrates the amplicon produced during the amplification of VNTR locus Mtb-v 10. Beginning location of VNTR 2,604,155. (All accession numbers are according to the H37Rv *M. tuberculosum* sequence done by the Sanger Institute.

(SEQ ID NO: 24)

ATCCTTGCAGGTGTTCGGTGGTGACGGTCGTGTTGTCGGCGGCTTCCAGG

CGCAACCGGAGGCGCCCAGCCCCACAATCAGTGCCAACAGTGCCAACAG

TGCCAACAGTGCCAGAATCGGGACGGCGCTACGCTGACGACGCACGTCAC

GAGCTTAGCGAAAACTGGGAATTTCCCCTACGTTTCATCAACGCCTCAGG

TGTCGATCCTAAAGCGCGGGTGCCGCCGGTATTCTTGCCCCAAATCGGTC

GGTTGACACCCGATGCGGTCGGCGAAGCCATCGGCATCGCGGCCGACGAC

ATCCCGATGGCGGCACGCTGGATCGGCA.GCCGACCATGCTCGCTCATCG

GCCAGCC

FORWARD PRIMER 5' GGAGGCGCCCAGCCCCACAA 3'

REVERSE PRIMER 5' TCAGGTGTCGATCCTAAAGCGCGGGTG 3'

EXAMPLE 7

This example illustrates the amplicon produced during the amplification of VNTR locus Mtb-v15 with primer pairs SEQ ID NO: 13 and SEQ ID NO: 14.

This example illustrates the amplicon produced during the amplification of VNTR locus Mtb-v15 with primer pairs SEQ ID NO: 13 and SEQ ID NO: 14. Beginning location of VNTR 3,238,462. (All accession numbers are according to the H37Rv *M. tuberculosum* sequence done by the Sanger Institute.

(SEQ ID NO: 25)

CCGCGCCGATCGGTTCCGTTGATCCGCGCTCCCCGCAGCCGCGCCGTCAG

ATCCGCGGGCCCGGCATCGTGGCGGCGCACAGCGCGGGGGTGGTGCACCC

GAACCTCGGTGATGGTCCGGCCGGTCACGTGAGCCTGCAAGCCGCGCCGC

ACCACCTCGACTTCGGGCAGCTCGGGCATCCAGTGATGATCGCAAGCGCG

GCGAAGCCGGGCGCAGCGGGTCATCACCATCGAACCAGTGATGATCGCA

AGCGCGGCGAAGCCGGGCGCAGCGGGTCATCACCATCGAACCAGTGATGA

TCGCAAGCGCGGCGAAGCCGGGCGCAGTCCCCCGCAAGCGGGAGGTGCC

CCCAGGTCATCACCATCGAACCAGTGATCATCGCAAGCGCGGCGAAGCC

GGGCGCAGTCCCCCCCAAGCGGGAGGTGCCCCCAGGTCATCACCATCG

AACCAGTGATGATCGCAAGCGCGGCGAACCCGGCCGCAGTCCCCCGCA

AGCGCGGCAAAGCCGGCGCCCCCAGGTCATCACCATCAATCCAGTTAGGC

GGAGGTTTTGCCCGGCATGGCGTTGTCGAGCACTTCCAGGGCTTTCCAAG

CGGCCGCCGCGGCTTTTTGCTCGGCTTCTTTTTTGGACCGGCCCACTCCT

GAAC

FORWARD PRIMER 5' GCGCCGCACCACCTCGACTT 3'

REVERSE PRIMER 5' GTTAGGCGGAGGTTTTGCCCGG 3'

EXAMPLE 8

This example illustrates the amplicon produced during the amplification of VNTR locus Mtb-v18 with primer pairs SEQ ID NO 15 and SEQ ID NO 16.

5' Beginning location of VNTR 4,227,024. (All accession numbers are according to the H37Rv *M. tuberculosum* sequence done by the Sanger Institute.

(SEQ ID NO: 26)

CGGGCTATCACCGGTTCATCTTCTGGGCCTATGGCCGCAACGGGGAGAGC

GATCCTCGGGTACTCGAGGCCATCCAAGTCCTCCGTATCCGCTATATCCT

GACCAGCACTCCGACGGTGCGGGGGTTTGCCGTGCCGGACGGACTAGTGT

CGTTAGAGACATCGAGGTCGTGGGCGAAGATCTACGACAACGGCGAGGCC

CGAATCTACGAATGGCGCGGCACTGCCGCAGCAACACACTCCTAGAAGGT

GCGTAAGAGGATGGTGATTGGATTGAGTACCGGCAGCGACGACGACGACG

TCGAGGTCATCGGCGGCGTCGACCCGCGGCTGATAGCGGTGCAGGAGAAC

GACTCCGACGAGTCGTCGCTGACCGACCTGGTCGAGCAGCCCGCCAAGGT

GATGCGCATCGGCACCATGATCAAGCAACTGCTCGAGGAGGTTCGCGCCG

CCCCACTCGACGAAGCCAGCCGCAATCGGCTACGCGATATCCACGCCACC

-continued

AGCATCCGCGAACTCGAAGATGGTCTGGCCCCGGAACTGCGCGAGGAGCT

CGACCGGCTTACCCTGCCGTTCAACGAGGACGCCGTGCCCTCGGACGCCG

AGTTGCGCATTGCCCAGGCACAGCTGGTCGGCTGGCTGGAAGGGCTGTTC

CACGGCATCCAAA

FORWARD PRIMER 5' ACAACGGCGAGGCCCGAATCTACGAA 3'

REVERSE PRIMER 5' ATAGGTGCGGTGGTCGTAGGCGC 3'

EXAMPLE 9

This example illustrates the amplicon produced during the amplification of VNTR locus Mtb-v20 with primer pairs SEQ ID NO 17 and SEQ ID NO 18. Beginning location of VNTR 23,693. (All accession numbers are according to the H37Rv *M. tuberculosum* sequence done by the Sanger Institute.

(SEQ ID NO: 27)

AGCGTATCCCGGGACCCGCGGGGATTCGGTGTAGCGGGTGTAGTCAGCGC

CGCCGCCATAGTCTTGCCGGCCGTATGTCGTGGCGCCTTGCTGGTAGCCC

TGGTCGTAACCGCCTTGGTCGGGGTAAGCCGGTCGTTGCTCGGGCGGGCC

GGAGGGCCAGAGGGCACATAGCTGCCCTCCTCGTGGCGAGCCGGGCCACG

CCCGTACTCCCCGTACCCGCCGTAGCCGGGCTGGCCGCCACCGGGTGAAG

GGCCGTAGCCGCCGCTTTGGCGATAGCCCTGGTCGTAGCCGGGAGCGCCG

TAGCCGGCAGCCGGGCCGGGAGAAACAGGAGGGCGTTGCTCGTAGGGCGG

CGGATAGCCCCCCTGCCCTTGGTCGGGGTAGCCTCGACCCTGGTCCTGGT

ACCCGCGCTGGTCGGGGTAGCCGCGTTGCTCGGGGTAACCGCGTTGCTCG

GGGTAACCGCCCTGGTCGGGGTACCCGATTTGCTCGGGGTAGTCGCCCTG

GTCCGGGTGGCGCGGGCGTGGGTAGCCCGGCTGGGGCGGGTAGCCGCCCG

TCTCGGGTGGATACCCCCCGCGGGGGTCAGATCCGCCTTGCGGATCCGGG

CCACCACGCGGATCCTCTTGCGGACGCGCATAGCGGTCGTCGTAATACTC

GTCGGGACGCCCCTGCCCCTGACCGCCACGGTAGCTCGAATTGTCACTCA

TTGGTGCTACTCCTGGTTCTGCGCCAAACGCGTGGTTTGATTGTGGCCGG

GCGCAATCGATGACCGGCGG

FORWARD PRIMER 5' CCCGGAGGGCCAGAGGGCACATAGC 3'

REVERSE PRIMER 5' GTCACTCATTGGTGCTACTCCTGGTTCTGCGC
CA 3'

While certain of the preferred embodiments of the present invention have been described and specifically exemplified above, it is not intended that the invention be limited to such embodiments. Various modifications may be made thereto without departing from the scope and spirit of the present invention, as set forth in the following claims.

References

1. Anonymous. 2002. Global Tuberculosis Control Report. World Health Organization. pg. 6

2. Bifani P J, M. B., Kurepina N E, Kreiswirth B N. 2002. Global dissemination of the *Mycobacterium tuberculosis* W family strains. Trends in Microbiology 10:45–52.

3. Braden, C. R., J. T. Crawford, and B. A. Schable. Assessment of *Mycobacterium tuberculosis* Genotyping in a Large Laboratory Network. Emerging Infectious Diseases. 8(11):1210–5, 2002 November.

4. Castro, K. G., and H. W. Jaffe. 2002. Rationale and methods for the national tuberculosis genotyping and surveillance network. Emerging Infectious Diseases. 8:1188–91.

5. Cowan, L. S., L. Mosher, L. Diem, J. P. Massey, and J. T. Crawford. 2002. Variable-Number Tandem Repeat Typing of *Mycobacterium tuberculosis* Isolates with Low Copy Numbers of IS6110 by Using Mycobacterial Interspersed Repetitive Units. Journal of Clinical Microbiology 40:1592–602.

6. Dale, J. W., D. Brittain, A. A. Cataldi, D. Cousins. J. T. Crawford, J. Driscoll, H. Heersma, T. Lillebaek, T. N. Quitugua, N. Rastogi, D. van Soolingen, V. Wright. 2001. Spacer oligonucleotide typing of *Mycobacterium tuberculosis*: recommendations for standardized nomenclature. Int. J. Tuberc. Lung Dis. 5:216–219.

7. Fang, Z., D. T. Kenna, C. Doig, D. N. Smittipat, P. Palittapongarnpim, B. Watt, and K. J. Forbes. 2001. Molecular evidence for independent occurrence of IS6110 insertions at the same sites of the genome of *Mycobacterium tuberculosis* in different clinical isolates. Journal of Bacteriology. 183:5279–52847.

8. Farlow, J., K. L. Smith, J. Wong, M. Abrams, M. Lytle, and P. Keim. 2001. *Francisella tularensis* strain typing using multiple-locus, variable-number tandem repeat analysis. Journal of Clinical Microbiology. 39:3186–92.

9. Frothingham, R., and W. A. Meeker-O'Connell. 1998. Genetic diversity in the *Mycobacterium tuberculosis* complex based on variable numbers of tandem DNA repeats. Microbiology 144:1189–96.

10. Kamerbeek J., L. S., A. Kolk, M. van Agterveld, D. van Soolingen, S. Kuijper, A. Bunschoten, H. Molhuizen, R. Shaw, M. Goyal, J. D. A van Embden. 1997. Simultaneous detection and strain differentiation of *Mycobacterium tuberculosis* for diagnosis and epidemiology. J. Clin. Microbiol. 35:907–914.

11. Keim, P., L. B. Price, A. M. Klevytska, K. L. Smith, J. M. Schupp, R. Okinaka, P. J. Jackson, and M. E. Hugh-Jones. 2000. Multiple-locus variable-number tandem repeat analysis reveals genetic relationships within *Bacillus anthracis*. Journal of Bacteriology. 182:2928–36.

12. Kremer, K., D. van Soolingen, R. Frothingham, W. H. Haas, P. W. Hermans, C. Martin, P. Palittapongarnpim, B. B. Plikaytis, L. W. Riley, M. A. Yakrus, J. M. Musser, and J. D. van Embden. 1999. Comparison of methods based on different molecular epidemiological markers for typing of *Mycobacterium tuberculosis* complex strains: interlaboratory study of discriminatory power and reproducibility. J. Clin. Microbiol. 37:2606–18.

13. Le Fleche P., M. Fabre, F. Denoeud, J. L. Koeck, G. Vergnaud. High resolution, on-line identification of strains from the *Mycobacterium tuberculosis* complex based on tandem repeat typing.2002. BMC Microbiology. 37:1–12.

14. Mazars, E., S. Lesjean, A. L. Banuls, M. Gilbert, V. Vincent, B. Gicquel, M. Tibayrenc, C. Locht, and P. Supply. 2001. High-resolution minisatellite-based typing as a portable approach to global analysis of *Mycobacterium tuberculosis* molecular epidemiology. Proceedings of the National Academy of Sciences of the United States of America. 98:1901–6.

15. Quitugua, T. N., B. J. Seaworth, J. Taylor, S. E. Weis, J. Gillete, I. Rosas, D. M. Magee, R. A. Cox. 2002. Transmission of drug resistant tuberculosis in Texas. Journal of Clinical Microbiology in press.

16. Rohlf, F. J. 2000. NTSYS-pc: numerical taxonomy and multivariate analysis system, 2.1 ed. Exeter Software, Setauket, N.Y.

17. Skuce, R. A., T. P. McCorry, J. F. McCarroll, S. M. Roring, A. N. Scott, D. Brittain, S. L. Hughes, R. G. Hewinson, and S. D. Neill. 2002. Discrimination of *Mycobacterium tuberculosis* complex bacteria using novel VNTR-PCR targets. Microbiology. 148:519–28.

18. Sola, C., I. Filliol, M. C. Gutierrez, I. Mokrousov, V. Vincent, and N. Rastogi. 2001. Spoligotype database of *Mycobacterium tuberculosis*: biogeographic distribution of shared types and epidemiologic and phylogenetic perspectives. Emerging Infectious Diseases. 7:390–6.

19. Sola, C., I. Filliol, E. Legrand, I. Mokrousov, and N. Rastogi. 2001. *Mycobacterium tuberculosis* phylogeny reconstruction based on combined numerical analysis with IS1081, IS6110, VNTR, and DR-based spoligotyping suggests the existence of two new phylogeographical clades. Journal of Molecular Evolution. 53:680–9.

20. Supply, P., S. Lesjean, E. Savine, K. Kremer, D. van Soolingen, and C. Locht. 2001. Automated high-throughput genotyping for study of global epidemiology of *Mycobacterium tuberculosis* based on mycobacterial interspersed repetitive units. Journal of Clinical Microbiology 39:3563–71.

21. Supply, P., J. Magdalena, S. Himpens, and C. Locht. 1997. Identification of novel intergenic repetitive units in a mycobacterial two-component system operon. Molecular Microbiology. 26:991–1003.

22. Supply, P., E Mazars, S. Lesjean, V. Vincent, B. Gicquel, and C. Locht. 2000. Varible human minisatellite-like regions in the *Mycobacterium tuberculosis* genome. Molecular Microbiology. 36:762–71.

23. van Embden, J. D., M. D. Cave, J. T. Crawford, J. W. Dale, K. D. Eisenach, B. Gicquel, P. Hermans, C. Martin, R. McAdam, and T. M. Shinnick. 1993. Strain identification of *Mycobacterium tuberculosis* by DNA fingerprinting: recommendations for a standardized methodology. J. Clin. Microbiol. 31:406–9.

24. Van Soolingen, D. 2001. Molecular epidemiology of tuberculosis and other mycobacterial infections: main methodologies and achievements. Journal of Internal Medicine. 249:1–26.

25. Weir, B. S. 1996. Genetic Data Analysis II: Methods for discrete population genetic data. Sinauer Associates, Inc., Sunderland, Mass.

We claim:

1. A pair of forward and reverse primers for amplification of VNTR located in DNA isolated from *Mycobacterium tuberculosum* species, said pair being selected from the group consisting of SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; and SEQ ID NO: 17 and SEQ ID NO: 18.

2. The pair of forward and reverse primers of claim 1, wherein a member of said pair further comprises an observable marker.

3. The pair of forward and reverse primers of claim 2, wherein said marker is a fluorescent label.

4. The pair of forward and reverse primers of claim 2, wherein said marker is a radioactive group.

* * * * *